(12) United States Patent
Egretier

(10) Patent No.: US 7,341,553 B2
(45) Date of Patent: Mar. 11, 2008

(54) DEVICE FACILITATING AND REINFORCING AN ERECTION OF THE PENIS

(75) Inventor: Jean Michel Egretier, Coursan (FR)

(73) Assignee: Benestar Aura, S.L. (ES)

( * ) Notice: Subject to any disclaimer, the term of this patent is extended or adjusted under 35 U.S.C. 154(b) by 464 days.

(21) Appl. No.: 10/471,948

(22) PCT Filed: Mar. 8, 2002

(86) PCT No.: PCT/FR02/00846

§ 371 (c)(1),
(2), (4) Date: Jun. 24, 2004

(87) PCT Pub. No.: WO02/074187

PCT Pub. Date: Sep. 26, 2002

(65) Prior Publication Data
US 2004/0236179 A1 Nov. 25, 2004

(30) Foreign Application Priority Data
Mar. 16, 2001 (FR) .................... 01 03649

(51) Int. Cl.
A61F 5/00 (2006.01)

(52) U.S. Cl. ........................................ 600/39
(58) Field of Classification Search ............ 600/37–41; 128/897–899, DIG. 25
See application file for complete search history.

(56) References Cited

U.S. PATENT DOCUMENTS

| 4,723,538 | A | * | 2/1988 | Stewart et al. ................. 600/41 |
| 4,960,113 | A | * | 10/1990 | Seeberg-Elverfeldt ....... 600/38 |
| 4,995,381 | A | | 2/1991 | Marmar et al. |
| 5,327,910 | A | | 7/1994 | Flynn |
| 5,344,459 | A | * | 9/1994 | Swartz .................... 623/14.12 |
| 5,997,469 | A | | 12/1999 | Northcutt |

FOREIGN PATENT DOCUMENTS

| DE | 36 06 126 A1 | 8/1987 |
| FR | 2 736 539 | 1/1997 |

* cited by examiner

Primary Examiner—Samuel G. Gilbert
(74) Attorney, Agent, or Firm—Black Lowe & Graham PLLC

(57) ABSTRACT

A device for facilitating and strengthening a penile erection consisting of a resilient ring which is deformable during the sexual act so as to act as a one-way valve due to tilting action to maintain blood pressure within the penis. The device is generally toroidal and is manufactured from a flexible material.

5 Claims, 1 Drawing Sheet

DEVICE FACILITATING AND REINFORCING AN ERECTION OF THE PENIS

CROSS-REFERENCE TO RELATED APPLICATIONS

Figure 1:
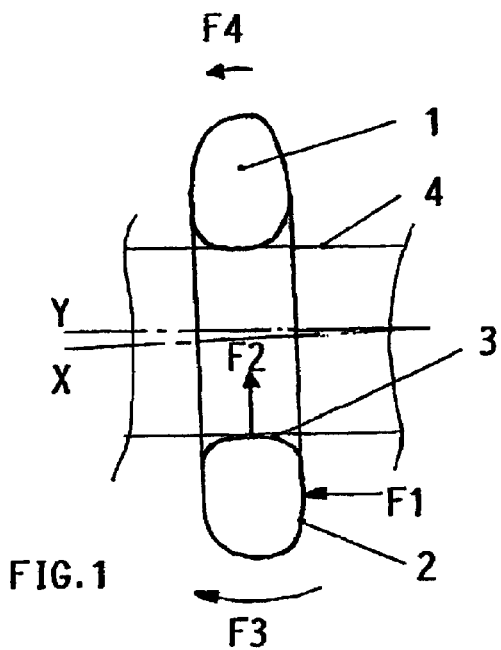

This application is a U.S. National Stage application of Patent Cooperation Treaty Application No. PCT/FR02/00846, filed Mar. 8, 2002, entitled DEVICE FACILITATING AND REINFORCING AN ERECTION OF THE PENIS, which itself claims priority from French patent application Ser. No. 01/03649 filed on Mar. 16, 2001 and claims priority from and the benefit of the date of said applications.

DESCRIPTION OF THE TECHNICAL FIELD

The invention refers to a device designed to facilitate and strengthen the penis erection through an initiating effect prior to the erection proper and pumping during the sexual intercourse.

BACKGROUND OF THE INVENTION

The erection mechanisms have as starting point a nervous centre located in the spinal cord (backbone). The brain has a modulating effect on the erection nervous centres. The fibres which innervate the penis come down the small pelvis and run along the edges of the seminal vesicles and the prostate (the cavernous nerves), then the membranous urethra. The cavernous nerves terminal branches innervate the cavernous bodies arteries and the smooth muscular fibres, thus controlling the penis tumescence (filling) and detumescence (coming back to the normal state).

The penis contains 3 structures allowing the erection because they contain erectile tissue: 2 cavernous bodies which are parallel cylinders located at the centre of the penis and the spongy body containing the urethra and which constitutes the essential of the glans. The erectile tissue is made of blood vessels rather loosely organized and surrounded by smooth muscular fibres. At rest, the penis is flaccid and the arrival of the blood in the cavernous body is reduced to the minimum because the blood vessels are contracted. When an erection occurs, the sexual excitation releases a nervous signal which carries the relaxation of the smooth muscle present around the blood vessels of the erectile tissue. The blood may then fill and dilate such vessels which are placed under pressure within the rigid wall of the cavernous bodies (the two cavernous bodies are surrounded by the albugineous tunique, a tough and not distensible wall). The veins prevent that the blood flows out which carries putting the penis under tension and in erection state. The stiffness of the erection depends then on the artery contribution and the effectiveness of the venous occlusion within the cavernous bodies. The detumescence occurs when the cavernous bodies venous drainage is re-established (new contraction by nervous stimulation).

The bulbo-cavernous and ischio-cavernous muscles assure, when being contracted an increase of the intra-cavernous pressure and therefore, the erection.

Three phenomena successively occur then:
the erectile tissue relaxation;
the vasodilatation and the increase of the arterial flow;
the blockade of the venous return under the albuginous tunique.

BRIEF SUMMARY OF THE INVENTION

The device according to the invention is the result of the anatomical and physiological analysis of the erection mechanisms.

Contrary to the well-known devices of the little or not elastic rings which fully block the blood return after the erection and which are located at the basis of the penis, the device according to the invention acts as a valve pump which, at each pressure (before the erection proper and when the partners are approaching each other) allows that the blood passes towards the penis strengthening thus its stiffness and, at each depression (spreading), it allows that the blood return is restrained.

Such effect has been obtained thanks to the shape provided to such device, its conception and its operation during the to and fro motions it sustains.

The device according to the invention, designed to facilitate and strengthen the penis erection, made of generally ring-shaped elastic material, adapted to be placed in the area at the basis of the penis and to exert a well-determined peripheral pressure on it is characterized:

in that its revolution body, which has a front face serving as supporting surface with the peripheral external vaginal area of the partner and an internal face serving as supporting surface with the penis comprises at the lower area a cylindrical fraction extending part the internal face of which comes as an extension to the lower internal face of such revolution body;

in that the material constituting the volume occupied by such revolution body and its extending part is adapted to transmit any negative deformation sustained, under the effect of a compression, by its front face in to a positive deformation of the lower internal wall of such body and its extending part which compresses thus the lower part of the penis;

in that the revolution body and its extending part carry out at each pressure on the lower front face, a back and tilt motion.

Such device is placed in the area of the basis of the penis leaving it a given freedom for moving in order that the pumping and braking effects are carried out fully free.

It is such motion associated to the deformation of the lower wall of the revolution body which allows to compress the lower part of the penis and to de-compress its top part and this in an alternative way.

The lower part of the revolution body can include a generally cylindrical fraction extension adapted by its internal face to extend the positive deformation of the lower wall of such device when contacting the lower part of the penis.

The characteristics and the advantages of the invention will more clearly appear when reading the detailed description below of at least a preferred embodiment of it given for no limiting example purpose and illustrated in the drawings attached.

Figure 2:
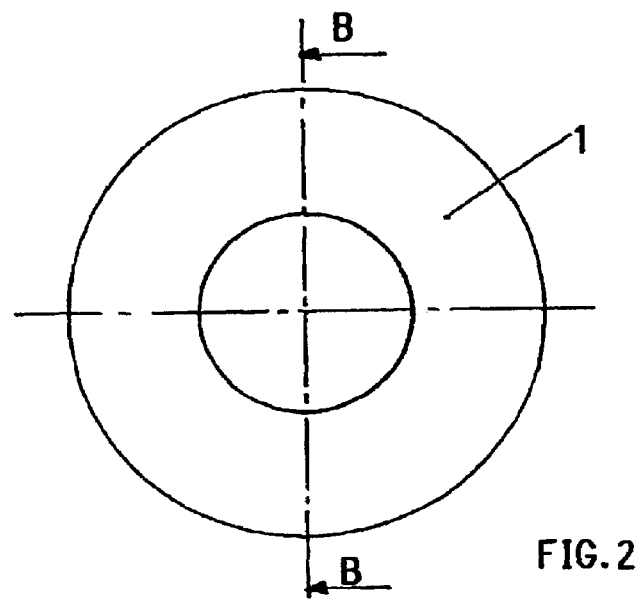
Figure 3:
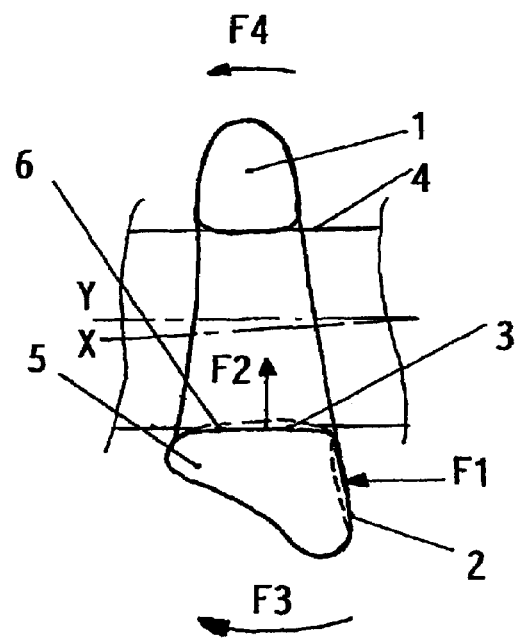
Figure 4:
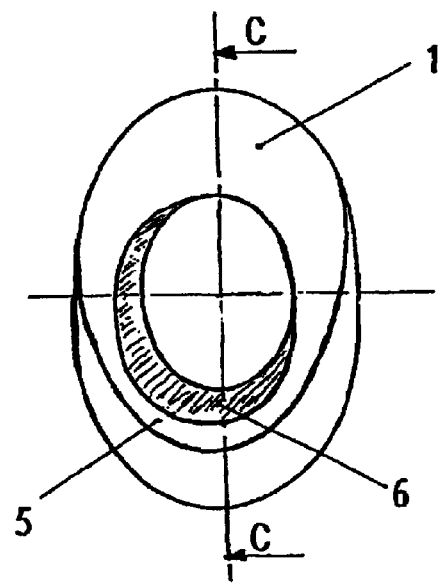

In such drawings:

BRIEF DESCRIPTION OF THE DRAWINGS the FIG. 1 is a lengthwise sectional view along the axis (BB) of the device according to the invention, the FIG. 2 is a front view of such basis device;

the FIG. 3 is a lengthwise sectional view along the axis (CC) of the device which include an extension:

the FIG. 4 is a view in perspective of such device.

DETAILED DESCRIPTION OF THE INVENTION

The device represented in the figures is designed to facilitate and strengthen the penis erection is made of a generally ring shaped elastic material and it is adapted to be placed in the area at the basis of the penis and to exert a well determined peripheral pressure on it.

Its revolution body (1) which shows a front face (2) serving as a supporting surface with the peripheral vaginal external area of the partner and an internal face (3) serving as supporting surface with the penis (4) includes at a lower area, an extending part (5), a cylindric fraction the internal face (6) of which is extending the lower internal face (3) of the revolution body (1).

The material constituting the volume occupied by such revolution body (1) and its extending part (5) is adapted to transmit any negative deformation sustained under the effect of a compression (F1) by the front face (2) and a positive deformation (F2) of the lower internal wall (3, 6) of such body (1) and its extending part (5) which compresses thus the lower part of the penis (4).

The internal face (6) of the extending part (5) extends the positive deformation of the internal wall of the device according to the invention.

The revolution body (1) and its extending part (5) carry out, at each pressure on the lower front face (2) a back and tilt motion according to the arrows (F3) and (F4).

For best using such device, the axis (X) of the opening of the internal surface (3) thereof is tilted backwards with relation to the axis (Y) tangential of the penis in the area of such opening.

Placing and starting it occur as follows:
- the body (1) is placed at the basis of the penis at rest at a 1 to 2 cm distance from its visible end;
- the backwards motion thereof carries the blood which inflates the upstream part which releases a nervous signal which makes the smooth muscle relay with therefore a start of filling the blood vessels of the downstream part of the cavernous bodies;
- the body (1) alternate tilt according to arrows (F3, F4) allows to initiate the erection phenomenon,
- the motion of such body during the sexual intercourse acts as a valve pump.

The narrowing of the internal diameter of such body is not aggressive and must not act as a tourniquet.

The device can be made of:
- a flexible material obtained by moulding or any other technique;
- by means of a pocket filled with air, liquid or any other flexible material, little or not compressible such as gel or some other.

The section of the body (1) can be egg-shaped.

Obviously, the invention is not limited to the embodiments disclosed and illustrated to which other variations can be provided, namely in:
- the shapes and sizes of the revolution body and its protuberance;
- the nature of the materials used;
- the techniques of embodiment of the device.

The invention claimed is:

1. Device designed to facilitate and strengthen a penis erection, made of generally ring-shaped elastic material, adapted to be placed in an area at a base of the penis and to exert a well-determined peripheral pressure on it, comprising in combination:
   a revolution body (1) having a front face (2) which when partners are approaching each other acts as a supporting surface with a peripheral vaginal external area of a partner and an internal face (3) serving as a supporting surface with the penis (4) including, at a lower area, an extending part (5), in general of a cylindrical fraction shape, the internal face (6) of which is extending beyond the lower internal face (3) of the revolution body (1);
   the material constituting the volume occupied by such revolution body (1) and said extending part (5) is adapted to transmit any negative deformation sustained under the effect of a compression (F1) by the front face (2) to a positive deformation (F2) of the lower internal wall (3, 6) of such body (1) and of its extending part (5) which compresses thus a lower part of the penis (4); in that an axis (X) of an opening of its internal surface (3) is tilt backwards with respect to an axis (Y) tangential to the penis in the area of such opening wherein the revolution body (1) and its extending part (5) carries out at each pressure on the lower front face (2) a back and tilt motion.

2. Device, according to claim 1, wherein it is made of a flexible material obtained by moulding it.

3. Device, according to claim 1 wherein it is made of a pocket full of air.

4. Device, according to claim 1 wherein the device is made of a pocket full of liquid.

5. Device, according to claim 1 wherein the device is made of a pocket full of a flexible material.

* * * * *